United States Patent [19]
Bjornson et al.

[11] Patent Number: 6,093,531
[45] Date of Patent: Jul. 25, 2000

[54] GENERATION OF HEMATOPOIETIC CELLS FROM MULTIPOTENT NEURAL STEM CELLS

[75] Inventors: Christopher R. Bjornson, Seattle, Wash.; Rod L. Rietze, Brunswick, Australia; Brent A. Reynolds, Saltspring, Canada; Angelo L. Vescovi, Milan, Italy

[73] Assignee: NeuroSpheres Holdings Ltd., Calgary, Canada

[21] Appl. No.: 09/100,679

[22] Filed: Jun. 19, 1998

Related U.S. Application Data

[60] Provisional application No. 60/060,289, Sep. 29, 1997.

[51] Int. Cl.[7] ..................................................... C12N 5/06
[52] U.S. Cl. ....................... 435/1.1; 435/325; 424/93.21
[58] Field of Search .................. 435/1.1, 325; 429/93.1, 429/93.21

[56] References Cited

U.S. PATENT DOCUMENTS

| | | | |
|---|---|---|---|
| 4,714,680 | 12/1987 | Civin | 435/347 |
| 5,061,620 | 10/1991 | Tsukamoto et al. | 435/7.21 |
| 5,589,376 | 12/1996 | Anderson et al. | 435/325 |
| 5,591,625 | 1/1997 | Gerson et al. | 435/366 |
| 5,635,386 | 6/1997 | Palsson et al. | 435/372 |
| 5,639,618 | 6/1997 | Gay | 435/7.21 |
| 5,646,043 | 7/1997 | Emerson et al. | 435/373 |
| 5,750,376 | 5/1998 | Weiss et al | 435/69.52 |

FOREIGN PATENT DOCUMENTS

WO 91/18620  12/1991  WIPO.

OTHER PUBLICATIONS

Orkin et al. report and recommendations of the panel to assess the NIH investment in research on gene therapy. www.nih.gov/news/panelrep.html, 1995.

Reynolds et al. generation of neurons and astrocytes from isolated cells of the adult mammalian central nervous system. Science vol. 255 pp. 1707–1710, 1992.

Bjornson et al. Turning brain into blood: A hematopoietic fate adopted by adult neural stem cells in vivo. Science vol. 283 pp. 534–537, 1999.

Zigova et al. The rising star of neural stem cell research. Nature Biotechnology vol. 16 pp. 1007–1008, 1998.

*Primary Examiner*—John S. Brusca
*Attorney, Agent, or Firm*—Burns, Doane, Swecker & Mathis, LLP

[57] ABSTRACT

Multipotent neural stem cell (MNSC) progeny are induced to generate cells of the hematopoietic system by placing the MNSC progeny in a hematopoietic-inducing environment. The hematopoietic-inducing environment can be either ex vivo or in vivo. A mammal's circulatory system provides an in vivo environment that can induce xenogeneic, allogeneic, or autologous MNSC progeny to generate a full complement of hematopoietic cells. Transplantation of MNSC progeny provides an alternative to bone marrow and hematopoietic stem cell transplantation to treat blood-related disorders.

16 Claims, 3 Drawing Sheets

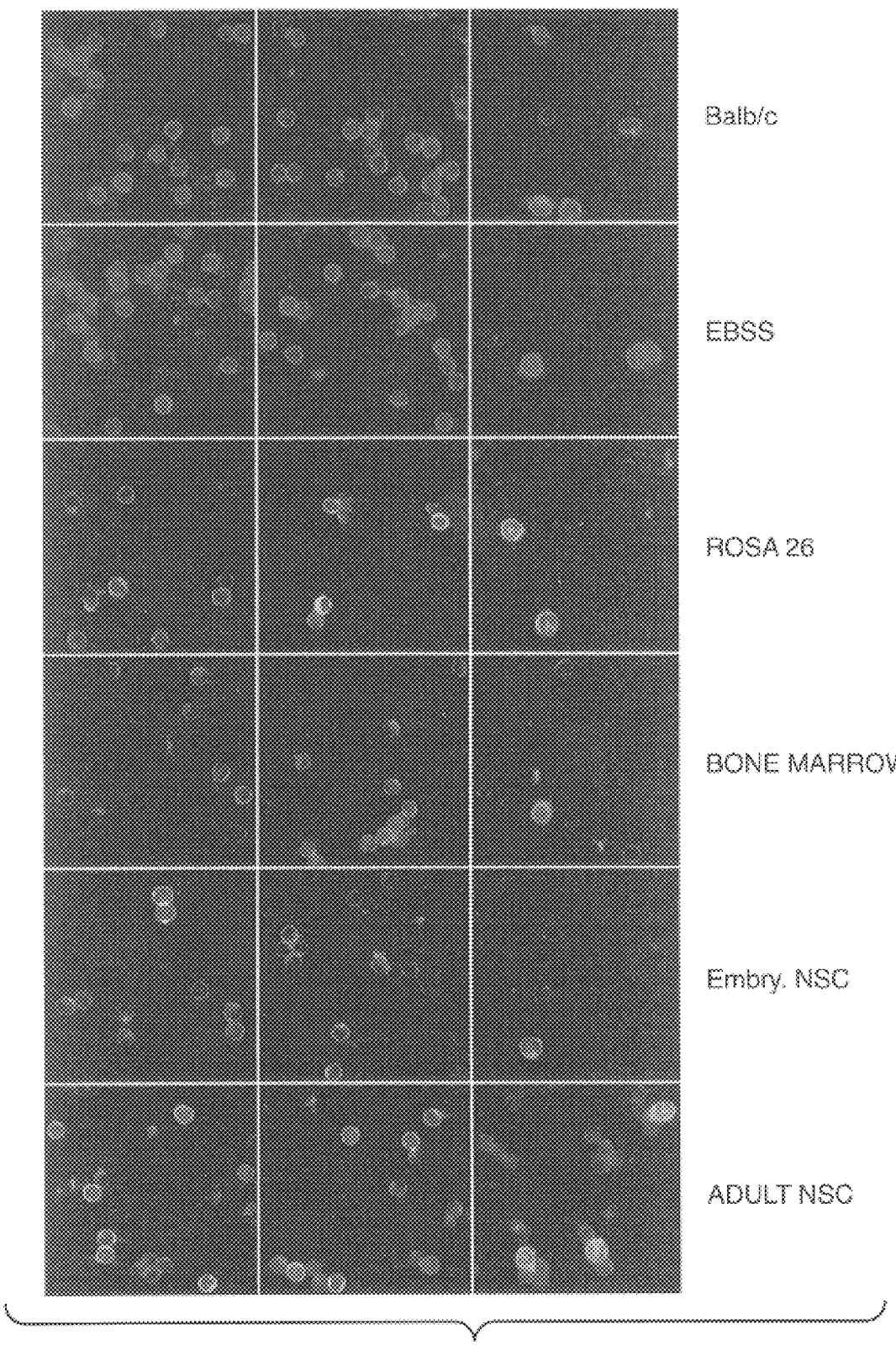
FIG._1

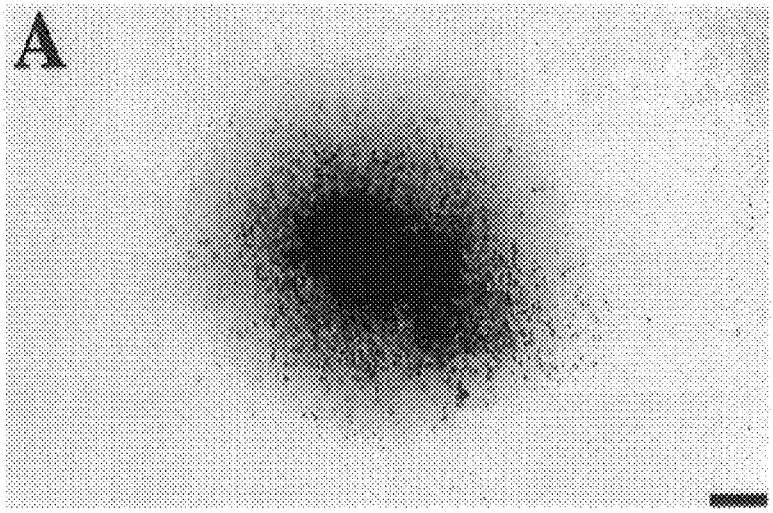
FIG._2A
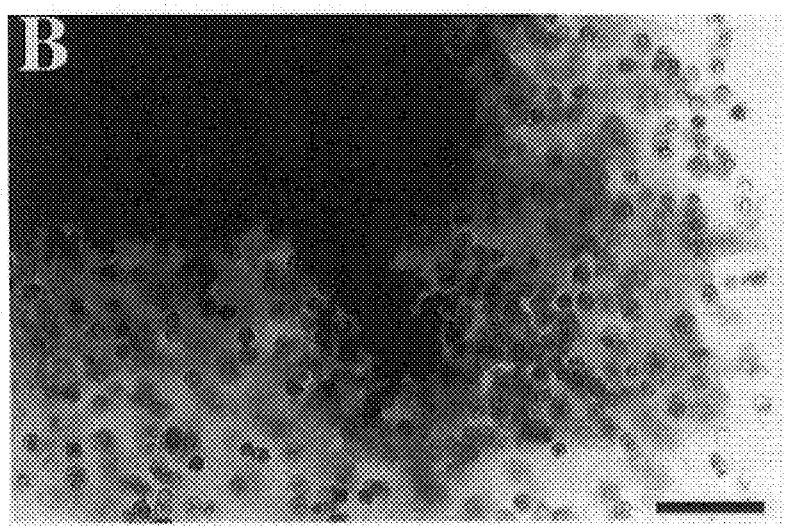
FIG._2B
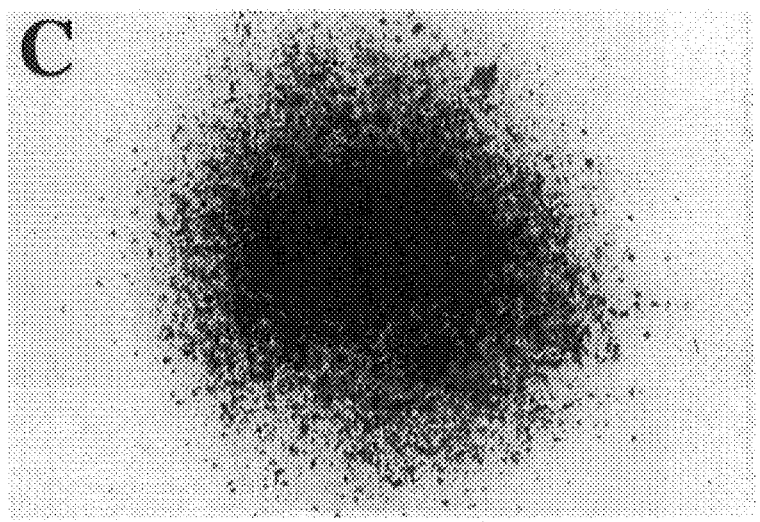
FIG._2C

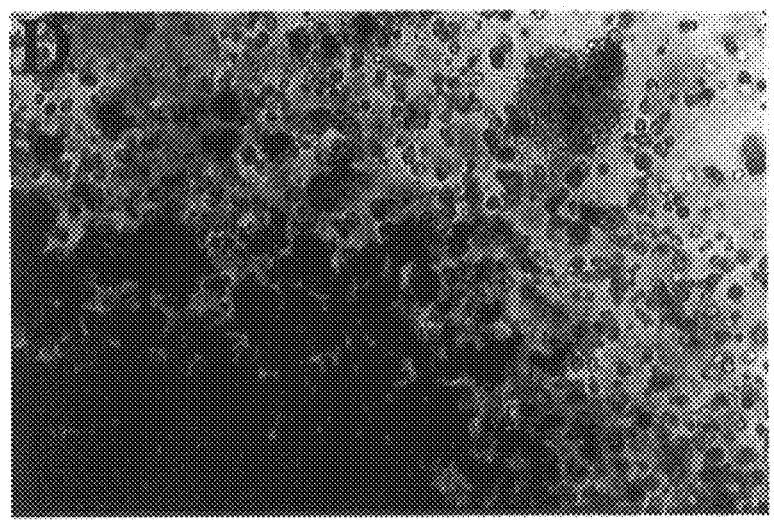
FIG._2D
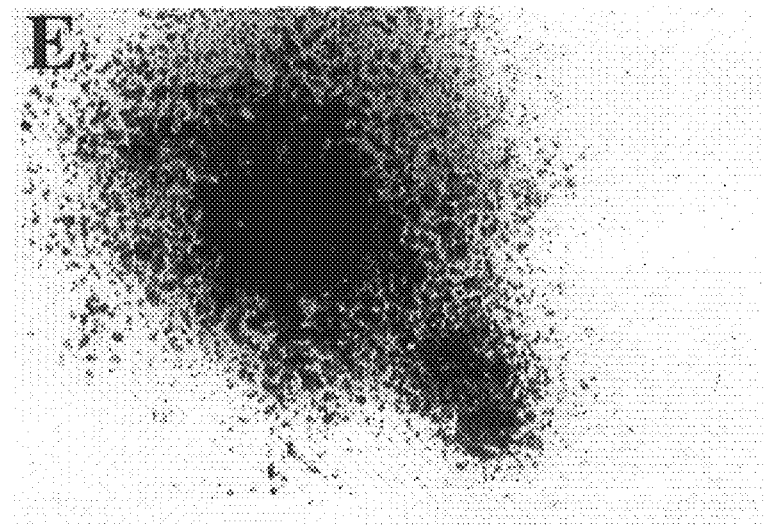
FIG._2E
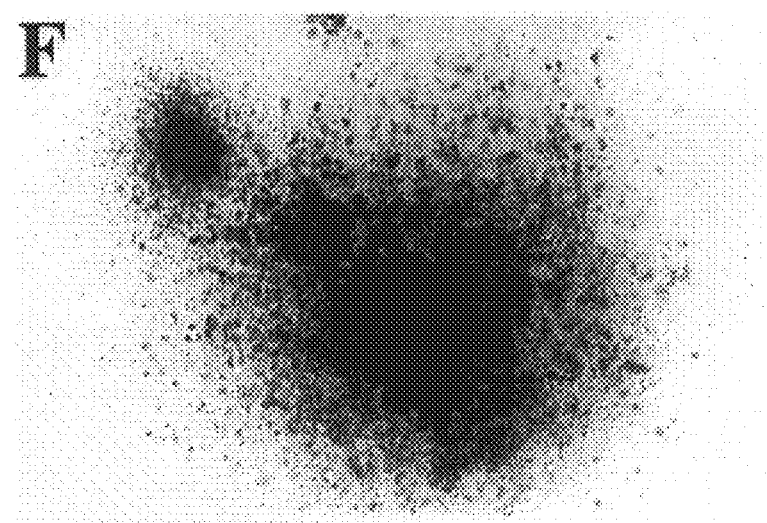
FIG._2F us 6,093,531

GENERATION OF HEMATOPOIETIC CELLS FROM MULTIPOTENT NEURAL STEM CELLS

RELATED APPLICATIONS

This application claims the benefit of U.S. Provisional Application Ser. No. 60/060,289, filed Sep. 29, 1997.

FIELD OF THE INVENTION

The field of the invention is directed towards the use of neural stem cell-derived compositions for repair, reconstitution, or augmentation of a mammals hematopoietic system.

BACKGROUND OF THE INVENTION

The use of hematopoietic stem cells and their progeny through bone marrow transplants to reconstitute the hematopoietic system has been employed to treat various blood-related diseases and disorders such as aplastic anemia, immune deficiencies and several forms of cancer including lymphomas and leukemias (see review in Lu et al. *Critical Rev. Oncol/Hematol.* 22:61–78 (1996)). Bone marrow transplantation is most commonly used in an attempt to restore hematopoietic function following exposure to myeloablative agents, for example after radiation therapy or chemotherapy in the treatment of a variety of cancers. These therapies, in addition to destroying the cancer, can also result in myelosuppression or myeloablation which, in turn, can lead to infection, bleeding disorders, and other complications. Recent estimates suggest that the need for transplantation of bone marrow-derived hematopoietic stem cells is growing at a rate of 20% per year and the market for the product is approximately $500 million per year (Strickland, D. *Bioworld Today* 8(14):1).

Unfortunately for patients, the use of bone marrow transplantation as a therapy is very restricted. Several disadvantages are inherent to the use of hematopoietic cells as a source of cells in the treatment of blood-related disorders and diseases. The success of an allogeneic transplant usually depends on finding a donor who is histocompatible with the recipient and willing to be subjected to the painful and time-consuming bone marrow donation process. Genetic incompatibility can lead to two common and potentially lethal complications. First, to decrease the chances of host versus graft reaction, the patient's immune system is compromised through the use of immunosuppressive drugs, leaving the patient highly susceptible to infection. Second, once the transplanted marrow cells are established they sometimes attack the patient in a graft versus host reaction. Combined, these two factors account for the major causes of non-autologous bone marrow transplant patient mortality and morbidity.

As an option to allogeneic transplantation, a patient's own bone marrow can sometimes be harvested and stored for later use assuming that the patient is healthy enough to withstand the procedure, and that the marrow is useful. Although the employment of such an autologous system generally precludes the danger of a genetic mismatch, serious risks still exist from possible undetectable contamination with malignant cells. The reliable detection and elimination of transformed marrow cells has yet to be accomplished. A further disadvantage with this approach is that only a limited amount of bone marrow cells capable of completely reconstituting the hematopoietic system can be harvested from an individual.

There has been much effort in establishing ex vivo culture systems for hematopoietic stem and progenitor cells for the purpose of generating a sufficient number of cells for transplantation purposes. However, the procurement of sufficient quantities of hematopoietic stem cells, either through bone marrow biopsy or from other sources, is a limitation to the use of this tissue for hematopoietic system related therapies. Present systems require complex culture conditions and tedious cell separation steps, and result in only a limited expansion of the numbers of hematopoietic stem cells. See, for example, U.S. Pat. No. 5,646,043, to Emerson et al. The biggest drawback is the lack of ability to sequentially passage the stem cells in vitro under defined culture conditions, over an extended period of time, in order to expand the numbers of functional cells available for transplantation. (Amos & Gordon, supra; Lu, et al., supra). As a consequence, there exists an ongoing need to either repeatedly harvest autologous stem cells or recruit compatible donors for therapies involving reconstitution of the hematopoietic system.

Due to the complications mentioned above, other sources of stem cells for hematopoietic reconstitution have been sought. Studies on the employment of fetal liver cells, neonatal spleen cells, or thymus cells have been reported. (Amos & Gordon, supra; Lu et al., supra). However, the ethical issues related to employing these cell types make the commercial use of them less attractive. The possibility of harvesting and cryopreserving cord blood is currently being studied, and may provide a more acceptable means of procuring cells for future use (Broxmeyer et al., (1989) *Proc. Nat. Acad. Sci. USA* 86:3828). To date, however, cord blood derived cells have only been shown capable of successfully repopulating the hematopoietic system of children (Amos & Gordon, supra). The recent identification of peripheral blood progenitor cells (PBPC) with marrow repopulating abilities has opened investigations into the use of PBPC for transplantation (reviewed in Lu et al., supra). Harvesting of these cells would potentially replace the need for bone marrow transplants. However, several disadvantages are apparent with this system: 1) the harvested blood may be contaminated, 2) the incidence of graft versus host disease is still very high, 3) many runs of leukapheresis are required to collect enough circulating stem cells for a complete hematopoietic reconstitution, and 4) collected stem cells cannot be held in an undifferentiated state for long periods of time.

It is apparent from the foregoing that alternatives are needed to present methods for reconstitution of a patient's hematopoietic system.

SUMMARY OF THE INVENTION

It is an object of the invention to provide compositions containing precursor cells derived from embryonic, juvenile or adult tissue and that can be readily obtained and used for the generation of hematopoietic cells for use in xenogeneic, allogeneic, or autologous transplantation. It is also an object of the invention to provide compositions that can be prepared using autologous cells that can be transplanted into a patient during or following myeloablative therapy for the treatment of blood-related disorders, such as lymphomas and leukemias, sickle cell disease, osteopetrosis and others, thus avoiding the risk of transplanting diseased or cancerous cells and overcoming the prior art problems of transplant rejections.

The present invention achieves these objectives by providing compositions containing multipotent neural stem cell progeny that can be used to generate hematopoietic cells. Thus, the invention provides a new medical use of multipotent neural stem cell progeny for the preparation of compositions for augmenting, treating, or altering a patient's hematopoietic system. A method for generating hematopoietic cells from mammalian multipotent neural stem cell progeny comprises placing the multipotent neural stem cell progeny in an environment, such as a patient's circulatory system, that induces the multipotent neural stem cell progeny to produce hematopoietic cells. The method can be used to treat a patient who is undergoing or has undergone myeloablative therapy, such as radiation therapy, chemotherapy, or a combination of both, and who thus has suppressed or depleted endogenous hematopoietic stem cells. The method can also be used to treat a patient afflicted with a genetic defect that affects hematopoietic cells, by transplanting multipotent neural stem cell progeny obtained from a donor with normal hematopoietic cells or, by administering genetically modified cells that can be autologous, allogeneic, or xenogeneic to the patient. In addition, the method can be used to treat normal patients to provide them with a supra-normal hematopoietic system or to provide them with a hematopoietic system with additional characteristics or functionalities over the normal state.

BRIEF DESCRIPTION OF THE DRAWINGS

FIG. 1: Direct visualization of engrafted multipotent neural stem cell (NSC) progeny using fluorescence microscopy. Spleen cell suspensions from control, non-irradiated ROSA26 and Balb/c (rows 1–3), and irradiated recipient mice (rows 4–6), were cytospun onto coverslips. Cells were double-labeled for both H-2K$^b$ and one of the hematopoietic phenotypic markers. Double-labeled cells were absent in the spleens of non-irradiated Balb/c mice (row 1) and in the spleens of EBSS injected control animals (row 2). An abundance of double-labeled cells were found in the ROSA26 non-irradiated control animals (row 3) as well as in animals injected with ROSA bone marrow (row 4) or embryonic NSC (row 5) or adult NSC (row 6). These findings show that the multipotent neural stem cell progeny have the ability to repopulate the compromised hematopoietic system. (Mag. 630×)

FIGS. 2A–2F: In vitro clonogenic assays of bone marrow derived from animals that received either embryonic or adult neural stem cells identify neural stem cell engraftment in the marrow. X-gal histochemistry was used to identify clones that were of neural stem cell origin. A large number of clones that formed from embryonic (A=50× mag.; B=200× mag.) or adult (C=50× mag.; D=200× mag,.) turned blue when exposed to X-gal for 8 hours. In the marrow of both embryonic (E) and adult (F) mice, there were a number of clones that did not turned blue when exposed to X-gal indicating a low level of early endogenous hematopoietic cell types. Scale bars are 100 μm (A, C, E & F) and 40 μm (B & D).

DETAILED DESCRIPTION OF THE INVENTION

The present invention lies in the significant discovery that multipotent neural stem cells (MNSCs) which can be obtained from embryonic and adult neural tissue, and which can be proliferated in vitro, as described in WO 93/01275 and in U.S. Pat. No. 5,750,376, are capable of generating hematopoietic progeny.

When a MNSC divides, it will give rise to a daughter MNSC, and thus is capable of self-maintenance. It can also give rise to a progenitor cell, which is an undifferentiated cell that is committed to give rise to a particular differentiative pathway. For example, a neuronal progenitor cell can divide a limited number of times; the resulting progeny then differentiate into neurons. Progenitor cells are usually capable of only a finite number of cell divisions prior to differentiation, and thus, unlike stem cells, are not capable of self-maintenance. The undifferentiated progeny of MNSCs, referred to herein as "precursor cells", include daughter MNSCs and committed progenitor cells.

The term "multipotent neural stem cell" ("MNSC") refers to a cell which is capable of extensive self renewal, i.e., is capable of replacing itself during cell division over an extended period of time, and is capable of generating all of the major cell types of the tissue in which it is located (i.e. neurons, astrocytes and oligodendrocytes). Using the culture methods described in U.S. Pat. No. 5,750,376, MNSCs can be induced to proliferate in vitro in a defined, growth factor-containing culture medium. The progeny of each MNSC can differentiate to generate astrocytes, oligodendrocytes, and neurons. The MNSCs can be continuously propagated in culture, to generate large numbers of progeny, without the need for transforming the cells with oncogenes or obtaining the cells from tumorigenic tissue. This makes the cells particularly desirable for therapeutic applications. The MNSC progeny can be stored until required using cryogenics or other methods known in the art.

The term "hematopoietic cell" refers to any type of cell of the hematopoietic system, including, but not limited to, undifferentiated cells such as hematopoietic stem cells and progenitor cells, and differentiated cells such as megakaryocytes, erythrocytes, leukocytes, granulocytes, monocytes, lymphocytes and natural killer cells.

When placed in an appropriate environment, such as those described herein, a MNSC can be induced to proliferate and generate progeny that differentiate into cells of the hematopoietic system. When reference is made herein to the environment in which MNSC progeny are placed, the common meaning of the term "environment" is intended. Thus, the term refers to the combination of external or extrinsic physical conditions that affect and influence the growth and development of multipotent neural stem cells and/or their progeny. The environment can be ex vivo or in vivo. Undifferentiated MNSC progeny, when transplanted into the circulatory system of a myeloablated mammal using the same transplantation techniques known in the art for bone marrow and hematopoietic stem cell transplantation, regenerate a full complement of the various blood cells and restore the mammal's hematopoietic system. Thus, a mammal's circulatory system is an example of an in vivo environment that induces MNSCs to generate cells of the hematopoietic system.

The transplantation of undifferentiated MNSC progeny has several advantageous over transplanting bone marrow or cultured hematopoietic stem cells. One advantage is that, when undifferentiated neural precursor cells are transplanted, the risk of graft-versus-host disease is substantially reduced because lymphoid cells are not transplanted. In addition, it is believed that MNSCs have reduced levels of, or missing, major histocompatibility complex (MHC) molecules on their surface. MHC molecules have been found to be absent from the surface of mouse MNSCs, and may be absent from the surface of MNSCs of other species as well. (see Motluk, A., New Scientist, p. 40 (1998)). In the case of autologous transplantation, another advantage of using MNSC progeny for repopulation of a patient's hematopoietic system, is that during or following chemotherapy or radiation therapy for treatment of leukemias and other blood-related disorders, the risk of re-introducing malignant or diseased hematopoietic cells is eliminated.

Another advantage of using MNSC progeny is that defined culture conditions, which have already been described in the literature, can be used to induce proliferation of MNSCs to readily generate a large number of MNSC progeny from a small amount of starting tissue. MNSCs can be obtained from embryonic, post-natal, juvenile or adult mammalian tissue. Any tissue that contains MNSCs can be used. Presently preferred is the use of neural tissue from any neural tissue that contains MNSCs including, but not limited to, the cerebral cortex, frontal lobe, conus medullaris, hypothalamus, cerebellum, midbrain, brainstem, spinal cord, cerebro spinal fluid, and tissue surrounding ventricles of the central nervous system (CNS). For autologous transplantation purposes, these tissues can be obtained by biopsy.

The MNSCs can be continuously proliferated in vitro and passaged to generate large numbers of cells for transplantation purposes using methods already known in the art. By comparison, prior methods for the in vitro generation of hematopoietic stem cells often require complex culture conditions and tedious cell separation steps, and result in only a limited expansion of the numbers of hematopoietic stem cells. For example, both U.S. Pat. No. 5,646,043 and U.S. Pat. No. 5,612,211, provide methods for a limited degree of in vitro hematopoietic stem cell renewal.

Suitable methods for obtaining and expanding MNSCs in culture for obtaining enriched populations of multipotent neural stem cells are disclosed in U.S. Pat. No. 5,750,376, which is incorporated herein by reference. As used herein, the phrase "enriched population of multipotent neural stem cells" means a population of cells that contains a higher percentage of MNSCs than that present in the tissue from which the MNSCs originated. Typically, less than about 0.1% of cells obtained from mammalian neural tissue are MNSCs. Therefore, an enriched population of MNSCs that contains about 1% MNSCs typically contains at least 10 times more MNSCs than that present in the neural tissue from which the MNSCs are derived. Secondary and subsequent MNSC cultures prepared according to the methods disclosed in U.S. Pat. No. 5,750,376, generally provide suitably enriched populations of MNSCs. For use in repopulating a patient's hematopoietic system, the enriched population of MNSCs, preferably comprises at least 1% MNSCs. More preferably, at least about 5% of the cells will be MNSCs. Still more preferred is the use of enriched population of MNSCs comprising at least 10% MNSCs. It is possible to obtain enriched populations of MNSCs comprising at least about 20% MNSCs. The use of highly enriched populations of MNSCs, containing at least 15%, or in some cases 20%, MNSCs may be desirable in that it may reduce the total number of cells needed for transplantation.

The percentage of MNSCs present in a culture can be estimated by passaging a known number of cells from the culture to fresh culture medium containing one or more growth factors that induces multipotent neural stem cell proliferation, such as epidermal growth factor (EGF) and fibroblast growth factor (FGF). The percentage of cells that form neurospheres indicates the approximate percentage of stem cells present in the culture. The term "neurosphere" refers to a cluster of precursor cells that forms when a MNSC is induced to proliferate in vitro. A neurosphere comprises the progeny of a single MNSC which includes daughter MNSCs and undifferentiated progenitor cells. U.S. Pat. No. 5,750,376 describes neurospheres in detail and provides photographs of neurospheres. Cell sorting techniques can be used to further enrich the cultures for MNSCs, by separating committed progenitor cells from MNSCs.

Undifferentiated MNSC progeny can be placed in a "hematopoietic-inducing environment", that induces their differentiation into hematopoietic cells. The term "hematopoietic-inducing environment" includes any ex vivo culture conditions or treatments, or any site in vivo of a host or patient, that induces MNSCs to generate hematopoietic cells. For ex vivo culture, depending on the desired phenotype, neural stem cell progeny can be induced to differentiate along a particular lineage through modification of the culture environment through the addition of one or more growth factors or cytokines or combinations thereof, and/or co-culture of the cells with cells from selected cell lines or feeder cells that provide a substratum and/or release extrinsic factors into the culture medium that influence the differentiative pathway of the MNSC progeny. In addition, manipulation of the substrate on which the cells are grown can influence the phenotypic outcome of a population of cells, either prior to transplantation or once transplanted. Culture techniques known in the art can be used to influence the differentiation of the MNSC progeny, such as those known to influence the differentiative fate of the progeny of early embryonic blastula stem cells. (see Keller, G. M. (1995) Curr. Opin. Cell Biol. 7:862–869). Thus, ex vivo techniques can be used to provide a population of MNSC progeny that is enriched for the presence of newly generated, undifferentiated or selectively differentiated progeny of the neural stem cells. The pretreated cells may be transplanted in the undifferentiated state, or alternatively, be differentiated or in the process of differentiating into specific cell types before being transplanted. Other culture conditions known in the art for culturing hematopoietic cells can be used, such as those described in U.S. Pat. Nos. 5,612,211 and 5,646,043.

Examples in vivo hematopoietic-inducing environments include a mammal's circulatory system, spleen, thymus, etc. For example, undifferentiated MNSC progeny that have been prepared using the procedures described in U.S. Pat. No. 5,750,376, may be systemically administered to a patient without further ex vivo manipulation. The patient's own circulatory system provides the environment that induces the MNSC progeny to generate cells of the hematopoietic system. The neural stem cells automatically repopulate lost or malfunctioning cell types in response to environmental signals. The MNSC progeny may also be administered to the circulatory system of a healthy mammal, and thus are used for the purpose of augmenting a normally functioning hematopoietic system. In this manner, the MNSC progeny serve as reserve supply of cells that remain undifferentiated until the time they are needed.

Another example of an in vivo hematopoietic-inducing environment is the circulatory system of a host animal. An enriched population of human MNSCs can be prepared using culture conditions known in the art, and systemically administered to a host mammal where the hematopoietic-inducing environment of the host aninal's circulatory system induces the MNSCs to generate cells of the human hematopoietic system. The human MNSCs may optionally be genetically modified, as discussed in more detail below, prior to administration into the host mammal. Additionally, the host mammal may optionally have had its endogenous hematopoietic system compromised prior to administration of the human MNSCs, for example, by radiation or any other suitable treatment. After a sufficient quantity of human hematopoietic cells have been generated in the host animal, they are removed and transplanted into a human patient.

When the host animal and the patient are different species, this process is called "xenoincubation".

Prior to transplantation, MNSC progeny can also be genetically modified to alleviate the symptoms of a specific disorder, or to endow new functions to the different progeny when implanted into individuals with no disorder. For example, the cells could contain a desired gene, such as a gene capable of expressing a missing protein, a disease-resistant protein or other beneficial protein. In contrast to the other stem cell systems, such as hematopoietic stem cell system, MNSCs can be induced to continuously divide under appropriate in vitro culture conditions, making them excellent targets for genetic modification. The term "genetic modification" as used herein refers to the stable or transient alteration of the genotype of a precursor cell by intentional introduction of exogenous DNA. The term also encompasses the masking or deletion of a harmful or undesired gene. DNA may be synthetic, or naturally derived, and may contain genes, portions of genes, or other useful DNA sequences. Methods for genetic modification of cells are well-known in the art, and methods for genetic modification of MNSC progeny are disclosed in U.S. Pat. No. 5,750,376. It may be desirable to genetically modify the MNSC progeny if they are to be used for transplantation into a patient to alleviate the symptoms of a specific disease with a genetic basis. The cells can be genetically modified before transplantation using an appropriate technique such as homologous recombination. For example, using techniques known in the art, neural stem cells can be transformed to express the allele of the chemokine receptor gene, CCR5, that confers immunity to HIV. The cells are then administered to an AIDS patient (who generally have a compromised hematopoietic system) and give rise to T-cells that are resistant to infection with HIV. (Paxton et al., *Nature Medicine* 2(4) :412–417 (1996); Liu Rong et al, *Cell* 86:367–377 (1996), and Samson et al., *Nature* 382:722–725 (1996)).

Bone marrow transplants have been used to treat a variety of diseases including, but not limited to aplastic anemia, deficiencies of the immune system, autoimmune diseases, cancers affecting the hematopoietic system, such as lymphomas and leukemias, sickle cell disease, osteopetrosis and others (see O'Reilly, R. J., *Blood* 62:941–964 (1983); Thomas, E. D. *Blood Cells*, 17:259–267 (1991); and Marmont, A. M. *Bone Marrow Transplant* 11:3–10 (1993)). Transplantation of MNSC progeny can be used in place of bone marrow for treatment of these diseases. In addition, intravenous administration of MNSC progeny into patients with autoimmune disorders, may alleviate the symptoms of the disorder. (see, Kenyon, N. S., *IBC on Hematopoietic Stem Cells* (1997)). MNSC progeny may also be altered by extrinsic or epigenetic means and implanted into normal or non-diseased individuals so as to endow them with a hematopoietic system with supra-normal functions.

Once suitable numbers of MNSC progeny needed for a particular purpose are obtained, they are transplanted into a patient using treatment regimes known to those skilled in the art for transplantation of hematopoietic stem cells. For the treatment of humans, much information is available in the art about techniques for the transplantation of hematopoietic stem cells for the treatment of various disorders (Bensinger et al. *J. of. Clin. Oncology*, 13(10):2547–2555 (1995); and Tricott et al., *Blood* 85(2):588–596). These references describe clinical trials for the transplantation of autologous peripheral blood stem cells for the reconstitution of a patient's hematopoietic system. These studies showed that infusion of approximately $2 \times 10^6$ to $5.0 \times 10^6$ CD34$^+$ cells per kilogram of patient, results in faster engraftment than when fewer CD34$^+$ cells are administered. Less than about 1% of unfractionated cells obtained from peripheral blood are CD34$^+$ (Lu et al., supra). It is estimated that approximately 1–5% of these CD34$^+$ cells are hematopoietic stem cells. By comparison, it is estimated that approximately 10–20% of sequentially passaged precursor cells propagated using the methods described in U.S. Pat. No. 5,750,376, are MNSCs. Thus, reconstitution of a patient's hematopoietic system using MNSC progeny should be possible using fewer cells than used in present methods. This is advantageous because the administration of fewer cells introduces less cryopreservant into the patient (assuming the transplanted cells were previously frozen). Another advantage is that less volume is administered to the patient, and can be delivered as a bolus dose, compared to the prolonged infusion required for the administration of peripheral blood stem cells (e.g. Bensinger et al., supra and Tricott et al., supra).

Approximately $10^2$ to $10^7$, and more typically, about $10^3$ to $10^6$ neural precursor cells/kg body weight should be sufficient for reconstitution of the hematopoietic system of a human patient who has undergone myeloablative therapy. The optimum number of cells can be determined using routine clinical trials. The number of cells needed may be different for a patient who has only a partially destroyed hematopoietic system. Clinical trials, similar to those described by Tricot et al., supra, and Bensinger et al., supra, can be used to determine appropriate treatment regimes for different patient populations.

The precursor cells are introduced to the recipient's circulatory system by a suitable method such as intravenous, subcutaneous, or intraperitoneal injection or infusion. Intravenous injection or infusion are the presently preferred methods. Generally, a composition will be prepared that comprises the precursor cells and a physiological solution, such as saline, which is suitable for use as a vehicle for the administration of the precursor cells to the circulatory system. The cells may first be rinsed in the solution to remove residual culture medium or, if the cells are freshly thawed, remove residual cryopreservation medium. If the MNSC progeny have been frozen, it is preferable to thaw them, culture them in vitro in a growth medium (i.e. a culture medium containing growth factors that induce MNSC proliferation), and passage them at least once prior to transplantation. This ensures the viability of the cells and removes excess cryopreservant. The final concentration of precursor cells is not critical, provided that a sufficient number of precursor cells are administered. For ease of administration and for the patient's comfort, it is usually preferred to minimize the total volume of cell suspension administered provided that the cells can be easily injected or infused into the patient without clumping. The final concentration will generally be in the range of about $10^7$ to $10^9$ precursor cells/ml. The physiological solution/precursor cell composition may additionally comprise hematopoietic growth factors such as granulocyte-macrophage colony-stimulating factor (GM-CSF) or granulocyte colony-stimulating factor (G-CSF) to accelerate the period in which certain cell types are generated. Alternatively, growth factors may be administered to the patient before or after the administration of the precursor cells. Prior to transplantation, a dosage form is prepared which comprises a device containing the precursor cell/physiological solution composition. The device can be any device that is suitable for delivery of the precursor cells to a patient. Such devices include, but are not limited to syringes, infusion bags, or like containers for intravenous administration of the precursor cell composition to a patient.

As detailed in Example 4 below using a mouse model, the transplantation of MNSC progeny into recipients subjected to total body irradiation so as to deplete functional hematopoietic stem cells, results in reconstitution of the hematopoietic system. It is believed that the procedure results in a permanent restoration of the hematopoietic system in most instances. However, with some disorders, repeated transplantations may be necessary.

It is apparent from the discussion herein and the Examples below that MNSC progeny provide an ideal alternative to the present use of hematopoietic stem cells for reconstitution of the hematopoietic system, or addition to the hematopoietic system, of an animal or human.

All cited references, patents, and patent applications, are incorporated herein by reference in their entireties. The following examples and drawings are for illustrative purposes only and are not to be construed as limiting the scope of the invention in any manner.

EXAMPLE 1

Obtaining MNSCs from Neural Tissue

A. Embryonic Tissue

Striatal tissue from the brains of 14-day-old CD1 and TGR-ROSA mice embryos (Charles River) was removed using sterile procedure. Tissue was mechanically dissociated with a fire-polished Pasteur pipette into serum-free medium composed of a 1:1 mixture of Dulbecco's modified Eagle's medium (DMEM) and F-12 nutrient (Gibco). Dissociated cells were centrifuged at 800 r.p.m. for 5 minutes, the supernatant aspirated, and the cells resuspended in DMEM/F-12 medium for counting.

B. Adult Tissue

Striatal tissue from the brains of adult TGR ROSA mice (these animals are genetically labeled with β-gal, allowing detection in host animals), RAG-1 mice (strain of "knockout" mice incapable of producing mature, functional B and T blood cells, negative control spheres), and C57BL/6J mice (background stock for RAG-1 knockouts). Stem cells from TGR ROSA and C57BL/6J animals, but not RAG-1 mice, should be able to reconstitute the B and T blood cell compartments of host animals. These tissues were removed and dissected into 500 μm sections and immediately transferred into low calcium oxygenated artificial cerebro spinal fluid (low $Ca^{2+}$ aCSF) containing 1.33 mg/ml trypsin, 0.67 mg/mil hyaluronidase, and 0.2 mg/ml kynurenic acid. Tissue was stirred in this solution for 90 minutes at 32° C.,–35° C. aCSF was poured off and replaced with fresh oxygenated aCSF for 5 minutes. Tissue was transferred to DMEM/F-12/10% hormone solution containing 0.7 mg/ml ovomucoid and triturated with a fire polished Pasteur pipette. Cells were centrifuged at 400 rpm. for 5 minutes, the supernatant aspirated and the pelleted cells resuspended in DMEM/F-12/10% hormone mix.

EXAMPLE 2

Preparation of Enriched Populations of MNSCs

Adult cells obtained from Example 1 were plated (1000 viable cells per plate) in noncoated 35 mm culture dishes (Costar) containing Complete Medium, 10 ng/ml bFGF and 20 ng/ml EGF [purified from mouse sub-maxillary gland (Collaborative Research) or human recombinant (Gibco/BRL)]. Embryonic cells, obtained using the methods described in Example 1, were grown in the same culture medium with the exception that bFGF was not added. Complete Medium is a serum-free medium composed of DMEM/F-12 (1:1) including glucose (0.6%), glutamine (2 μM), sodium bicarbonate (3 mM), and HEPES (4-[2hydroxyethyl]-1-piperazineethanesulfonic acid) buffer (5 mM) (all from Sigma except glutamine [Gibco]). Complete Medium is supplemented with a defined hormone mix and salt mixture (Sigma) that includes insulin (25 μg/ml), transferrin (100 μg/ml), progesterone (20 nM), putrescine (60 μM), and selenium chloride (30 nM). The murine MNSCs present in the cultures proliferated giving rise to neurospheres.

After 6–7 days in vitro the neurospheres were allowed to settle in the bottom corner of the flask. The neurospheres were then transferred to 50 ml centrifuge tubes and centrifuged at 300 rpm for 5 minutes. The medium was aspirated off, and the neurospheres were resuspended in 1 ml of the proliferation medium in which they were grown. The neurospheres were dissociated with a fire-narrowed Pasteur pipette and triturated to form a single cell suspension. The cells were counted and replated at 50,000 cells/ml in Complete Medium. New neurospheres formed after a few days. This proliferation/passaging process was performed four times.

EXAMPLE 3

Preparation of Clonally-derived MNSC Progeny

The cells of neurospheres, obtained from adult ROSA striatal tissue using the methods described in Examples 1 and 2, were diluted to approximately 1 cell per well in a 96 well (200 μl growth medium/well) tissue culture plate to generate clonally derived MNSC progeny. The presence of a single cell in a well was confirmed with phase contrast microscopy. Single neurospheres developed in about 20% of the wells, indicating that each of these wells contained a single MNSC which proliferated to form the neurosphere. The neurospheres were passaged as described in Example 2. After several passages, neurospheres were collected for transplantation at approximately four days after formation.

EXAMPLE 4

Regeneration of Hematopoietic System Using MNSCs

Equal numbers of male and female adult Balb/c mice 2.5 to 3 months old (25–30 g, Charles River) were subjected to total body irradiation (850 rads), to severely deplete functional hematopoietic stem cells. Irradiation procedures essentially followed those described by Tarbel et al., *Development* 121:4077–4083 (1987) and Down et al., *Blood* 3:661–669 (1991). Due to the incidence of gastrointestinal and pulmonary toxicity reported in the literature following single doses of 850 rads, a fractionated dose of 450 rads followed by 400 rads 4 hours later was used, resulting in the cumulative absorbed dose by the soft tissue being approximately 850 rads. During irradiation, the animals were continuously monitored for movement via video cameras. Several measures were taken to assure that all regions of the body received equal amounts of irradiation: 1) mice were placed in a Lucite cage with dimensions that prevented the animals from crawling over one another (which could vary the dose received), 2) each fraction of the total dose was applied with the cobalt source first in a dorsal then a ventral position, and 3) calibration detection devices were taped to the top, bottom and walls of the container as well as to the dorsal aspect of one animal and the ventral aspect of a second animal in each group to accurately measure the precise dose received by each group of animals. In each case, the calibration devices employed determined that the actual dose received by the different groups of animals was 850 rads ±2%.

Several batches of enriched MNSC populations, prepared as in Examples 2 and 3, were resuspended in EBSS (Earle's balanced saline solution) at room temperature. The cells were then kept at 4° C. until just prior to transplantation when they were warmed to body temperature to avoid temperature shock to the recipient animal.

A portion of the irradiated mice ("recipient mice") were injected with an enriched population of MNSCs prepared as in Example 2 or 3 above, approximately 16 hours following the completion of the second irradiation event. The investigators responsible for monitoring and assaying the irradiated mice were not informed of the contents of each vial of cells, nor of the recipient versus control animals. The recipient mice were administered (via tail vein injection) 0.2 ml of an enriched population of MNSCs in warm (body temperature) EBSS. Control mice received warm EBSS alone or murine fibroblasts (approx. $10^6$ 3T3 cells). As a positive control, some of the recipient mice received an injection of freshly obtained ROSA bone marrow cells (approx. 27,000,000 cells).

Prior to transplantation, some batches of MNSCs were exposed to cytokines. The cytokine pretreatment consisted of: stem cell factor (10 ng/ml), interleukin (IL)-1alpha (2 ng/ml), IL-2 (10 ng/ml), IL-3 (5 ng/ml), and IL-6 (10 ng/ml). This pretreatment was administered to the cells 24 hours before the cells were injected into the recipient animal.

As susceptibility to infectious agents is a problem following exposure to lethal whole body irradiation, several measures were taken to address this. The animals started to receive antibiotics (neomycin sulfate, 1 mg/ml, added to water) 48 hours before irradiation and their drinking water was acidified (pH 3.5–4.0) to reduce bacterial flora in the gut. The mice were housed in filtered cages, in rooms designed to safely house immunodeficient animals, and provided with sterilized food and water. Finally, laboratory personnel wore gowns, gloves, caps and masks when working with the animals.

Irradiated mice were observed daily with body weight, coat condition, eye appearance, motility and general posture monitored and recorded every second day in an effort to track physiological condition. Animals exhibiting a loss of appetite, decreased mobility, diarrhea or severe loss of weight were euthanized by cervical dislocation and had their blood and organs assayed for hematopoietic cell types and engraftment where appropriate) through immunohistochemical and fluorescent activated cell sorting (FACS) analysis as described below. All animals that died prematurely were autopsied to determine their cause of death.
Results:

Table I shows the results of the numbers of animals that survived each treatment.

TABLE I

| TREATMENT | Animals per Condition | Surviving Animals (6 months post transplantation) |
| --- | --- | --- |
| No Injection | 4 | 0/4 |
| EBSS | 30 | 8/30 |
| Murine Fibroblasts 1,000,000 cells | 5 | 1/5 |
| Adult ROSA Bone Marrow | 10 | 10/10 |

TABLE I-continued

| TREATMENT | Animals per Condition | Surviving Animals (6 months post transplantation) |
| --- | --- | --- |
| 27,000,000 cells Adult ROSA MNSC progeny cytokine pretreatment 350,000 cells | 5 | 5/5 |
| Adult ROSA MNSC progeny no cytokines 500,000 cells | 5 | 5/5 |
| Embryonic CD1 MNSC progeny no cytokines 2,000,000 | 2 | 2/2 |
| Embryonic CD1 MNSC progeny cytokine pretreatment 750,000 cells | 2 | 1/2 |

The majority of MNSC progeny and bone marrow recipient animals survived the treatment (more than 6 months) while the majority of the negative control animals (those receiving fibroblasts, saline, or no injection following irradiation) did not survive for periods greater than 30 days. Autopsies performed on negative control animals revealed unusually small or, on occasion, absent spleens and/or thymus glands, indicative of a severely compromised hematopoietic system. Consistent with this condition was the presence of small, gray colored livers in those control mice with the longest survival times, suggesting a significant loss of red blood cells. In sharp contrast, the surviving MNSC recipient mice appeared to be healthy and active over a prolonged period of observation (up to 15 months).

To test for the engraftment of donor cells, peripheral blood was collected from the survivors 7 to 11 months after transplantation and subjected to flow cytometric, FACS analysis, and PCR amplification of the Lac Z gene. β-galactosidase was detected in a number of hematopoietic cell types suggesting that the complete reconstitution of all major hematolymphatic lineages had occurred.

Flow Cytometric Analysis

At 7 to 11 months following the completion of the tail vein injection procedure (with the study still being performed using a "double-blind" format), peripheral blood was harvested from representative mice of each condition and assayed for the presence of β-gal activity and hematopoietic surface antigen expression (Berger et al. *J. Cytometry*, 17:216–223 (1994)). To facilitate the detection of β-gal$^+$ hematopoietic cell types, the FluoroReporter lac-Z flow cytometry kit (Molecular Probes #F-1931) was employed. Basically, viable hematopoietic cells are loaded via hypotonic shock with a fluorogenic beta galactosidase substrate fluorescein di-beta-D-galactopyranosidase (FDG). Non-fluorescent FDG is sequentially hydrolyzed by β-galactosidase so as to produce highly fluorescent fluorescein, which is readily detectable by flow cytometric analysis. Due to the hypotonic loading of FDG, cell surface antigens remain intact and propidium iodide exclusion to assay for viability can still be used. This procedure indicated the presence of β-gal positive cells in the peripheral blood of recipient mice. Backgating of the β-gal positive cells in mice that had been repopulated with ROSA bone marrow or MNSC progeny, revealed a similar pattern of distribution, suggesting similar cell types were being produced in both animals.

In addition to the lacZ gene, ROSA 96 cells express a MHC type 1 molecule (denoted as H-2 type in the mouse) different from the Balb/c hosts (H-2K$^b$ and H-2K$^d$ respectively). Therefore it was possible to monitor the presence and resultant phenotype of MNSC progeny in transplanted animals using immunocytochemistry. To detect engraftment, various hematopoietic tissues (including blood) from transplanted and control animals were processed for flow cytometry using H-2K$^d$ ant H-2K$^b$ antibodies to detect different H-2 isotypes. Antibodies employed were CD4 (#09005A), CD11b (01715B;), CD19 (09655B), and H-2K$^b$ (06105A), all as phycoerythrin (PE) conjugates, biotinylated H-2K$^b$ (06102D) and H-2K$^d$ (06092D) and mouse IgG$_{1a}$,κ (isotype control) all from Pharmingen (San Diego, Calif.). All primary antibodies were used at 1:50. Streptavidin FITC conjugate (Jackson Laboratories; Mississauga, ON) was used at a dilution of 1:100. All animals used to generate data had survived a minimum of 6 months post-irradiation.

Cell suspensions from spleen and thymus were prepared in EBSS by cutting the organ into small pieces then grinding between two frosted Corning slides. Bone marrow was flushed from the femurs with EBSS. Erythrocytes were lysed in 144 mM NH$_4$Cl, 17 mM Tris-Cl, pH 7.2, for 4 minutes at room temperature. Cells were rinsed with FACS buffer (EBSS+1.0% fetal calf serum), centrifuged at 1100 rpm for 7 minutes and resuspended in FACS buffer before counting. For antibody staining, 50 µl of antibody solution was mixed with 50 µl of cell suspension (1.0×10$^6$ cells) and incubated at 4° C. for 30 minutes. Cells were rinsed in FACS buffer, centrifuged at 1100 rpm for 5 minutes, resuspended in 50 µl FACS buffer and incubated with 50 µl of secondary antibody (where appropriate) at 4° C. for 30 minutes. Finally, cells were rinsed in FACS buffer, centrifuged, and resuspended in 500 µl of EBSS for flow cytometric analysis. Isotype controls were used to set gates whenever biotinylated antibodies were employed. In the case of directly labeled antibodies, gates were set using cells alone. Immediately prior to flow cytometric analysis, propidium iodide was added to control suspensions to ensure a viability of >95%. Flow cytometric analysis was performed on a FACScan (Becton-Dickinson), with all events gated on the forward/side scatter, to quantify the number of H-2K$^{b+}$ cells relative to the total number of events gated (n=6, ±S.E.M.; p<0.05). The results are shown in Table II below.

TABLE II

|  | Peripheral Blood | Spleen | Bone Marrow |
|---|---|---|---|
| Non-irradiated Balb/C control, No transplantation | 2.35 ± 0.40 | 0.92 ± 0.15 | 2.26 ± 0.55 |
| Non-irradiated ROSA26 control, No transplantation | 94.2 ± 1.13 | 97.3 ± 1.03 | 42.3 ± 4.09 |
| Irradiated Balb/C control EBSS injection only | 1.68 ± 0.43 | 1.68 ± 0.44 | 1.59 ± 0.51 |
| Irradiated Balb/C ROSA26 bone marrow transplant | 56.7 ± 12.6 | 95.3 ± 2.45 | 38.8 ± 2.48 |
| Irradiated Balb/C Adult ROSA26 MNSC progeny transplant | 43.1 ± 6.87 | 65.4 ± 23.5 | 35.8 ± 10.0 |
| Irradiated Balb/C Embryonic ROSA26 MNSC progeny transplant | 43.9 ± 6.98 | 96.5 | 22.0 |

Dot plots were prepared of H-2K$^b$ versus H-2k$^d$ positive cells in peripheral blood and H-2K$^b$ labeled CD4 (T-cells), CD19 (B-cells), or CD11b (granulocytes) positive hematopoietic cell types in spleen cell suspensions of unirradiated control (ROSA26, Balb/c) and irradiated recipient animals. H-2K$^b$ positive cells were detected in the spleen and peripheral blood of animals that had received either ROSA bone marrow or MNSC progeny. No H-2K$^b$ positive cells were found in animals injected with EBSS alone. In neural and hematopoietic stem cell recipients, H-2K$^b$ positive cells were also found in other hematopoietic tissues including the bone marrow and thymus. Populations of each of the differentiated phenotypes (which represent all of the terminally differentiated hematopoietic cell types with the exception of erythrocytes) were found double-labeled with the H-2Kb antigen in the spleen of hematopoietic and MNSC recipients.

Further immunocytochemical analysis of H-2K$^b$ positive cells in MNSC progeny recipients revealed the presence of T lineage cells (H-2K$^{b+}$/CD8$^1$; H-2K$^{b+}$/Cd3e$^+$), B lineage cells (H-2K$^{b+}$/B220$^+$; H-2K$^{b+}$/IgM$^+$; H-2K$^b$/IgD) granulocytic lineage cells (H-2K$^{b+}$/CD 89$^+$) and myeloid lineage cells (H-2K$^{b+}$/Mac-3$^+$) evidencing that MNSC progeny generated all the major hematopoietic cell lineages.

TABLE III

|  | CD3e/H-2K$^b$ | CD11b/H-2K$^b$ | CD19/H-2K$^b$ |
|---|---|---|---|
| Non-irradiated Balb/C control, No transplantation | 0.52 ± 0.08 | 0.47 ± 0.09 | 0.57 ± 0.08 |
| Non-irradiated ROSA26 control, No transplantation | 33.0 ± 5.16 | 30.0 ± 2.24 | 51.0 ± 1.90 |
| Irradiated Balb/C control EBSS injection only | 0.77 ± 0.05 | 0.43 ± 0.02 | 0.59 ± 0.07 |
| Irradiated Balb/C ROSA26 bone marrow transplant | 31.9 ± 2.62 | 14.5 ± 3.85 | 56.2 ± 2.50 |
| Irradiated Balb/C Adult ROSA26 MNSC progeny transplant | 28.1 ± 14.2 | 14.9 ± 10.9 | 26.8 ± 11.7 |
| Irradiated Balb/C Embryonic ROSA26 MNSC progeny transplant | 40.6 | 8.71 | 31.0 |

Table III shows the percentage of ROSA26 (H-2K$^{b+}$) cells in the spleens of transplanted and control animals that were double labeled for the hematopoietic specific antigens CD3e (T-cells), CD11b (granulocytes) and CD19 (B-cells) as assayed by flow cytometry, 7 to 11 months after transplantation. A significant number of double-labeled cells were found in animals injected with ROSA26 bone marrow, embryonic neural stem cells (NSCs) and clonally derived adult NSCs. All percentages are calculated relative to the total number of events gated (n 6, ±S.E.M.; p<0.05).

To further confirm the flow cytometric results, the same samples were cytospun onto coverslips and visualized using fluorescence microscopy. To accomplish this, cells which were first prepared for flow cytometric analysis (see above) were fixed using 4% paraformaldehyde/0.1% gluteraldehyde in a 1:1 ratio for 10 minutes at room temperature. Cells were then cytospun onto coverslips precoated with 10% rat albumin (Gibco BRL) at 700 rpm for 8 minutes at room temperature. Coverslips were mounted using Fluorosave (Calbiochem, La Jolla, Calif.) and visualized using a Zeiss Axioscop fluorescence microscope.

The results are shown in FIG. 1. All of the differentiated hematopoietic lineages were observed in irradiated animals that received EBSS, yet none of the cells expressed the H-2K$^b$ antigen. In animals that received ROSA26 derived bone marrow, all of the differentiated phenotypes were observed with a substantial portion of these cells expressing H-2K$^b$. A similar result was observed in animals that received MNSC progeny, demonstrating that MNSC transplantation can replace bone marrow transplantation. Cells double-labeled with H-2K$^b$ and either CD4, CD11b, or CD19 were visualized in animals that received MNSC progeny prepared according to Examples 2 and 3.

To qualitatively identify engraftment of neural stem cells into earlier hematopoietic lineages, the bone marrow of MNSC and bone marrow transplanted animals was isolated for use in in vitro clonogenic assays. Cells isolated from the bone marrows were diluted to a density of 500 cells/mL in IMDM supplemented with 2% HIFBS (Gibco BRL). Cells were added to MethoCult (Stem Cell Technologies Inc) as per the manufacturer's specifications, supplemented with the appropriate cytokines, in a 1/10 v/v ratio and 1.1 mL was dispensed into 35 mm dishes and left for 10–14 days at 37° C. in a 5% $CO_2$ atmosphere. Cytokines used were: Interleukin-3 (10 ng/mL,), Interleukin-7 (10 ng/mL), stem cell factor (50 ng/mL), erythropoietin (3 U/mL) (R&D Systems) and Interleukin-6 (10 ng/mL; Novartis). X-gal histochemistry was used to detect β-galactosidase activity in clones of neural stem cell origin. X-gal working solution, comprised of 5 mM $K_3F3(CN)_6$, 5 mM $K_4Fe(CN)_6 3H_1O$, 2mM $MgCl_2$ (Sigma) and X-gal (in dimethyl sulfoxide; Molecular Probes) to a final concentration of 1 mg/mL in PBS (pH 7.4), was added to methylcellulose cultures 10–14 days after plating.

Cultures were exposed to 400 μL of X-gal working solution for 8 hours at 37° C.

Pictures were taken using Kodak ektachrome 400 slide film using a Canon Epoh camera mounted to an inverted Zeiss Axiophot microscope. Under control conditions, none of the colonies derived from Balb/c bone marrow turned blue while the majority of ROSA26 clones did. Bone marrow isolated from animals that received either embryonic or adult stem cells gave rise to colonies of cells that turned blue when exposed to X-gal (FIGS. 2A–2D), suggesting that neural stem cells can give rise to both early as well as late hematopoietic cells. There were a number of clones isolated from animals that received either adult or embryonic neural stem cells that did not turn blue when exposed to X-gal (FIGS. 2E & 2F). This is likely due to the presence of endogenous bone marrow cells that were not eliminated as a result of irradiation. The identities of these clones appeared to encompass a broad spectrum of early cells.

FDG β-gal detection performed in combination with immunocytochemistry showed the presence of T lineage cells (β-gal$^+$ CD4$^+$; β-gal$^+$ CD8a$^+$; β-gal$^+$ CD3e$^+$), B lineage cells (β-gal$^+$ B220$^+$; β-gal$^+$ IgM$^+$; β-gal$^+$ IgD$^+$), granulocytic lineage cells (β-gal$^+$ CD89$^+$) and myeloid lineage cells (β-gal$^+$ Mac-1$^+$), evidencing that MNSCs generated all the major hematolymphatic lineages.

To identify possible engraftment by neural stem cells, the presence or absence of lacZ in DNA isolated from the spleens of animals transplanted 7 to 12 months earlier using PCR was assayed. The primer dropping method described previously (H. Wong, W. D. Anderson, T. Cheng K. T. Riabowol, Anal Biochem. 223, 251 (1994)) was used to amplify genomic DNA using; the polymerase chain reaction. Briefly, 10 μg of genomic DNA was digested overnight using EcoRI] and 0.5μg was used as PCR template. 40 cycles of 94° C. (1 minute), 60° C. (1 minute) and 72° C. (1 minute) was used to amplify lacZ using an appropriate primer pair. After 20 cycles, primers specific for glyceraldehyde-3-phosphate dehydrogenase (GAPDH) were added as an internal control.

LacZ was not detected in animals that received vehicle EBSS. By comparison, animals that received ROSA26 bone marrow produced a very strong signal. LacZ was also detected in animals transplanted with ROSA MNSC progeny. This appeared to be independent of cell source as animals injected with either embryonic or adult (including clonally derived adult) neural stem cell progeny produced a strong signal. To eliminate the possibility of a false negative result, the gene encoding GAPDH was co-amplified with lacZ in the same reaction tube. The presence of a weakly amplified GAPDH signal under all conditions indicated that the lacZ amplification was genuine.

Further analysis included Southern blot analysis, reverse transcription-polymerase chain reaction (RT-PCR) and genomic-PCR of harvested tissues to identify $\geq$-gal$^+$ cells in the peripheral blood.

EXAMPLE 5

Capacity of MNSCs to Maintain Hematopoietic System

The ability of the MNSCs to generate new hematopoietic stem cells is determined by extracting bone marrow from surviving, radiation-treated animals from Example 4 that received labeled cells of neural origin, and injecting the prepared bone marrow cells into recipient, irradiated animals in which the endogenous hematopoietic stem cells have been severely depleted or destroyed. The recovery of the irradiated animals and the presence of labeled cells in the recipients' bone marrow indicates that the bone marrow transplant contained viable hematopoietic stem cells which were originally derived from neural tissue.

EXAMPLE 6

Treatment of Immune Deficiency

Mice that carry a germline mutation in a recombination activating gene (RAG-1), have a total inability to produce mature B or T lymphocytes (Mombaerts et al., Cell 68:869–877 (1992). The immune system of these mutant mice can be described as that of non-leaky SCID (severe combined immunodeficiency) mice. RAG-1 breeding stocks (strain C57BL/6J-Rag1$^{bn1Mom}$) can be obtained from Jackson Laboratories (#JR2216).

MNSC progeny were prepared as described in Examples 1 and 2 using neural tissue obtained from RAG-1 mice and from the background strain C57BL/6J mice (Jackson #664) which do not have the RAG-1 mutation. Using the methods described in Example 4, approximately 1,000,000 C57BL/6J precursor cells were injected intravenously into the prewarmed tail vein of the RAG-1 pups prior to 3 weeks of age. Beginning 4–6 weeks post-injection, blood was harvested from the recipient animals, and assayed for the detection of serum CD3e (T-cell receptor); Mombaerts et al., supra. The presence of CD3e indicates the presence of mature T lymphocytes, which are cells not normally found in RAG-1 mice. Additionally, the presence of IgM and IgD, which indicate the presence of mature B lymphocytes, which are also cells not normally found in RAG-1 mice, can also be assayed; Mombaerts et al., supra. A sub-population of those animals which test positive for these mature cell types were sacrificed at different time points following injection and examined for evidence of hematopoiesis.

Results:

When tested using FACS analysis, the blood of experimental RAG-1 animals, which had received C57BL/6J MNSC, showed positive results for CD3e, a marker for the T-cell receptor found on functional T cells. In contrast, the blood of the mice which had received either RAG-1 or EBSS had negative results for the CD3e marker. This demonstrates that MNSC transplantation can be used to treat genetic defects of the hematopoietic system.

EXAMPLE 7

Allogeneic Transplantation to Treat Genetic Defects

Healthy MNSC progeny are prepared from normal neural tissue obtained from a biopsy of a human donor and proliferated in vitro using procedures known in the art in order to obtain an enriched population of human multipotent neural stem cells. The MNSC progeny are transplanted into a consenting patient with a genetic disease of the hematopoietic system, such as, but not limited to sickle cell anemia. The patient is administered the MNSC after receiving chemotherapy or radiation therapy to deplete the patient's hematopoietic stem cell population. The cells are administered intravenously over a 24–48 hour period, at a dose of $1 \times 10^2$ to $5 \times 10^6$ cells/kg. The optimal time course of administration and numbers of cells to be administered may need to be modified above this number in some cases. The MNSCs are administered 36–48 hours after the last dose of chemotherapy or radiation therapy. Selected growth factors and/or cytokines known to promote hematopoiesis (GF-CSF or G-CSF at a dose of 250 $\mu g/m^2$/day) may be administered following the infusion until successful engraftment is established. Successful engraftment will be deemed to have occurred with the patient's neutrophil count is greater than $0.5 \times 10^9$ and $0.5 \times 10^9$ cells/L on two consecutive days and when the patient's platelet count is greater than $20 \times 10^9$/L for 7 consecutive days. Prophylactic antibiotics are given when the absolute neutrophil count is less than $0.5 \times 10^9$ cells/L (oral ciprofloxain (500 mg twice a day) or oral penicillin VK (250 mg every 6 hours) or intravenous acyclovir (5 mg/kg every 8 hours).

Depending on the ability to match the host and donor tissue, immunosuppressant drugs may be administered to prevent rejection reactions.

EXAMPLE 8

Autologous Transplantation to Treat Genetic Defects

MNSC progeny are prepared from neural tissue obtained from a biopsy of a patient afflicted from a genetic disorder that affects the blood cells. The patient's MNSCs are proliferated in vitro using procedures described in U.S. Pat. No. 5,750,376, to obtain an enriched population of multipotent neural stem cells. The MNSC progeny are genetically modified using procedures known to correct the genetic defect. For example, U.S. Pat. No. 5,760,012, describes methods to genetically modify hematopoietic stem cells in patients afflicted with hemoglobinopathies such as sickle cell anemia, beta-thalassemia, or Gaucher's Disease. Methods of treating sickle cell anemia are disclosed by Cole-Strauss, A., et al. (*Science,* 273:1386–1389 (1996)). The same methods can be used to genetically modify a patient's MNSCs.

The genetically modified MNSC progeny are transplanted into the patient. In same cases, it may be desirable to first treat the patient with chemotherapy or radiation therapy to deplete the patient's diseased hematopoietic stem cell population. The genetically modified MNSCs are administered intravenously using the methods described above in Example 8.

EXAMPLE 9

Allogeneic Transplantation to Confer Resistance to HIV

MNSC progeny are prepared from neural tissue obtained from a biopsy of human donor having the CCR5 allele that has been shown to confer resistance to HIV infection (Samson et al., supra) and proliferated in vitro using procedures known in the art in order to obtain an enriched population of human multipotent neural stem cells. Using the procedures described in Example 7, the MNSC progeny are transplanted into a patient infected with HIV to prevent or reduce progression of AIDS. Alternatively, the MNSC progeny can be transplanted into a non-infected patient to confer immunity or resistance to HIV infection.

EXAMPLE 10

Autologous Transplantation to Confer Resistance to HIV

Neural tissue is obtained from a patient infected with HIV. Using procedures described in U.S. Pat. No. 5,750,376, MNSCs present in the neural tissue are proliferated in vitro. The MNSC progeny are genetically modified using techniques known in the art to replace the endogenous CCR5 gene with a CCR5 allele that has been shown to confer resistance to HIV infection (Samson et al., supra). The genetically modified MNSC progeny are transplanted into the patient using the procedures described in Example 7.

EXAMPLE 11

Autologous Transplantation for Chemotherapy Patients

Prior to undergoing high dose chemotherapy, a neural tissue biopsy is performed on a patient and the MNSCs are expanded in vitro and stored using procedures described in U.S. Pat. No. 5,750,376. The cells are infused into the patient after the chemotherapy treatment using the methods described in Example 7. Immunosuppressant drugs should not be required.

EXAMPLE 12

Xenoincubation of MNSCs to Produce Hematopoietic cells for Reinfusion into Donor Species Human embryonic MNSCs, obtained from the diencephalon of a fetus or an adult are expanded in vitro using methods described in U.S. Pat. No. 5,750,376. After several passages, cells from 1-week old neurospheres are obtained. Approximately $1 \times 10^6$ cells are injected into the tail veins of irradiated RAG-1 mice, as outlined in Example 4.

The animals are allowed to survive and blood is harvested at regular intervals to demonstrate that human MNSC are able to repopulate the mouse hematopoietic system. The ability of human neural stem cells to reconstitute the hematopoietic system of mice, indicates that MNSCs can be injected into other species of mammals, in particular larger animals such as pigs and horses, where the MNSCs orchestrate the production of new human blood cells which can be harvested for use in human patients.

All references, patents, and patent applications cited herein are incorporated by reference.

What is claimed is:

1. A method of generating hematopoietic cells from mammalian multipotent neural stem cell progeny comprising placing said multipotent neural stem cell progeny in an environment that induces said multipotent neural stem cell progeny to produce said hematopoietic cells, wherein said environment comprises a mammal's circulatory system and said multipotent neural stem cell progeny are administered to said circulatory system.

2. The method of claim 1 wherein said multipotent neural stem cell progeny are derived from juvenile or adult tissue.

3. The method of claim 1 wherein said multipotent neural stem cell progeny are derived from embryonic or fetal tissue.

4. The method of claim 1 wherein said multipotent neural stem cell progeny are derived from neural tissue selected from the cerebral cortex, frontal lobe, conus medullaris, hypothalamus, cerebellum, midbrain, brainstem, spinal cord, cerebro spinal fluid, and tissues surrounding CNS ventricles.

5. The method of claim 1 wherein prior to administering said multipotent neural stem cell progeny to said circulatory system, said mammal undergoes a treatment to suppress or deplete endogenous hematopoietic cells.

6. The method of claim 5 wherein said treatment is radiation.

7. The method of claim 5 wherein said treatment is chemotherapy.

8. The method of claim 1 wherein said multipotent neural stem cell progeny are derived from said mammal.

9. The method of claim 1 wherein said multipotent neural stem cell progeny are derived from an allogeneic donor.

10. The method of claim 1 wherein said multipotent neural stem cell progeny are derived from a xenogeneic donor.

11. The method of claim 1 wherein said multipotent neural stem cell progeny comprise an enriched population of multipotent neural stem cells.

12. The method of claim 11 wherein said enriched population of multipotent neural stem cells comprises at least 1% multipotent neural stem cells.

13. The method of claim 11 wherein said enriched population of multipotent neural stem cells comprises at least 10% multipotent neural stem cells.

14. A dosage form for generating new hematopoietic cells in a patient comprising a device containing a composition comprising multipotent neural stem cell progeny, wherein said device is suitable for delivering said composition to a patient's circulatory system.

15. The dosage form of claim 14, wherein said device comprises a syringe for intravenous injection.

16. The dosage form of claim 14, wherein said device comprises a bag for intravenous infusion.

* * * * *